(12) United States Patent
Eek

(10) Patent No.: US 12,144,844 B2
(45) Date of Patent: Nov. 19, 2024

(54) TREATMENT OF INTERNAL DISC DISRUPTION AND CONNECTIVE TISSUE INJURIES

(71) Applicant: Bjorn Eek, Lake Forest, CA (US)

(72) Inventor: Bjorn Eek, Lake Forest, CA (US)

( * ) Notice: Subject to any disclaimer, the term of this patent is extended or adjusted under 35 U.S.C. 154(b) by 243 days.

(21) Appl. No.: 17/656,926

(22) Filed: Mar. 29, 2022

(65) Prior Publication Data

US 2023/0066890 A1    Mar. 2, 2023

Related U.S. Application Data

(62) Division of application No. 17/465,738, filed on Sep. 2, 2021, now Pat. No. 11,318,187.

(51) Int. Cl.
| | |
|---|---|
| *A61K 38/18* | (2006.01) |
| *A61K 31/167* | (2006.01) |
| *A61K 47/02* | (2006.01) |
| *A61K 47/26* | (2006.01) |
| *A61K 47/38* | (2006.01) |

(52) U.S. Cl.
CPC ........ *A61K 38/1841* (2013.01); *A61K 31/167* (2013.01); *A61K 38/1825* (2013.01); *A61K 47/02* (2013.01); *A61K 47/26* (2013.01); *A61K 47/38* (2013.01)

(58) Field of Classification Search
CPC .............. A61K 38/1841; A61K 31/167; A61K 38/1825; A61K 47/02; A61K 47/26; A61K 47/38; A61K 9/0019; A61K 31/7008; A61K 31/728; A61K 31/737; A61L 2300/414; A61L 2400/06; A61L 2430/38; A61L 27/20; A61L 27/54
See application file for complete search history.

(56) References Cited

U.S. PATENT DOCUMENTS

| | | |
|---|---|---|
| 7,744,651 B2 | 6/2010 | Trieu et al. |
| 8,048,865 B2 | 11/2011 | Eek |
| 9,555,084 B2 * | 1/2017 | Bartorelli ........... A61K 38/1858 |
| 10,603,522 B2 | 3/2020 | Diederich et al. |
| 2003/0229049 A1 | 12/2003 | Eek |
| 2005/0282774 A1 | 12/2005 | Eek |
| 2007/0227547 A1 | 10/2007 | Trieu |
| 2008/0103564 A1 | 5/2008 | Burkinshaw et al. |
| 2011/0003770 A1 | 1/2011 | Eek |
| 2011/0312913 A1 | 12/2011 | Eek |
| 2012/0295867 A1 | 11/2012 | Eek |
| 2014/0066389 A1 | 3/2014 | Eek |
| 2014/0271870 A1 | 9/2014 | O'Shaughnessey et al. |
| 2016/0074479 A1 | 3/2016 | Serbousek et al. |
| 2016/0310520 A1 | 10/2016 | Eek |
| 2017/0151276 A9 | 6/2017 | Eek |
| 2018/0169137 A1 | 6/2018 | Erwin |

FOREIGN PATENT DOCUMENTS

| | | | |
|---|---|---|---|
| WO | 2001066130 A1 | 9/2001 | |
| WO | WO-03041724 A1 * | 5/2003 | ........... A61K 31/728 |
| WO | 2007136673 A2 | 11/2007 | |
| WO | 2008012511 A1 | 1/2008 | |
| WO | 2014149270 A1 | 9/2014 | |
| WO | 2017075719 A1 | 5/2017 | |

OTHER PUBLICATIONS

Li et al. "Action of fibroblast growth factor-2 on the intervertebral disc", Arthritis Research & Therapy vol. 10 No 2.
Bao-Gan Peng, "Pathophysiology, diagnosis, and treatment of discogenic low back pain", WJO www.wjgnet.com, Apr. 18, 2013 vol. 4, Issue 2.
Zhang et al. "Toxicity Effects of Methylene Blue on Rat Intervertebral Disc Annulus Fibrosus Cells", www.painphysicianjournal.com. Journal Article; (Journal Article) , vol. 22, Issue: 2, pp. 155-164.
Riester et al. "RNA sequencing identifies gene regulatory networks controlling extracellular matrix synthesis in intervertebral disk tissues"; Journal of Orthopaedic, vol. 36, Issue: 5, pp. 1356-1369, 2018.
Wang et al. Basic fibroblast growth factor attenuates the degeneration of injured spinal cord motor endplates; Neural Regeneration Research; vol. 8, Issue 24, Aug. 2013.
Walsh et al. "Glucosamine HCl alters production of inflammatory mediators by rat intervertebral disc cells in vitro"; The Spine Journal; vol. 7; pp. 601-608; 2007.
Chu et al. "In Vitro Exposure to 0.5% Bupivacaine Is Cytotoxic to Bovine Articular Chondrocytes"; The Journal of Arthroscopic and Related Surgery, vol. 22, No. 7 Jul. 2006: pp. 693-699.
Xu et al. Expression of transforming growth factor and basicfibroblast growth factor and core protein ofproteoglycan in human vertebral cartilaginousendplate of adolescent idiopathic scoliosis'; https://pubmed.ncbi.nlm.nih.gov/16135988/.

\* cited by examiner

*Primary Examiner* — Marcela M Cordero Garcia
(74) *Attorney, Agent, or Firm* — Procopio, Cory, Hargreaves & Savitch LLP; Brent A. Johnson; Erica A. Spence

(57) ABSTRACT

This disclosure relates to treating internal disc disruption or a connective tissue injury. The treatment involves injecting, or otherwise administering, a therapeutic composition into an animal, such as a human being, in need thereof. The therapeutic composition may contain transforming growth factor beta 1 (TGF-β1) or transforming growth factor beta 2 (TGF-β2), fibroblast growth factor (FGF), and a pharmaceutically acceptable excipient or a secondary agent.

17 Claims, No Drawings

TREATMENT OF INTERNAL DISC DISRUPTION AND CONNECTIVE TISSUE INJURIES

CROSS-REFERENCE TO RELATED APPLICATIONS

This application is a divisional of application Ser. No. 17/465,738, filed Sep. 2, 2021, which is incorporated by reference herein in its entirety.

FIELD

This disclosure relates to therapeutic compositions and methods for treating internal disc disruption and/or connective tissue injuries.

BACKGROUND

Low back pain is a common affliction affecting up to 80% of people during the course of their lives. Most pain is short-lived and mild to moderate. However, for many it is a serious medical and social problem. De Palma et al found that the prevalence of low back pain was zygapophyseal joints 31%, sacro-iliac joints 18%, and lumbar discs 42% (the remainder being non-specific).

Disc degeneration is first seen in the early teens. The numbers increase with each passing year. The prevalence of disc degeneration younger than 50 years is 71% men and 77% women. Disc degeneration unto itself is not a painful condition. It becomes painful when there is motion segment instability caused by postural and physical stress that causes weakening of the annular portion of the disc leading to nerve irritation within the outer annulus and disc perimeter, then degeneration, disc space narrowing with development of a thickened posterior joint capsule, and later a disc osteophyte complex. The ligamenta flava becomes thickened and redundant. The facet joints gradually overlap, causing hypertrophy of the facet joint capsules, and later arthrosis, often trapping sensory and sympathetic nerves in the joint capsule leading to facet joint pain. Spinal stenosis often is the end result. This is properly termed Degenerative Disc Disease (DDD), which is variably painful.

The concept of Internal Disc Disruption (IDD) was first introduced by Henry V. Crock, an orthopedic surgeon, in 1970 in a paper titled "A reappraisal of the intervertebral disc lesions" published in the Medical Journal of Australia. This condition is caused by severe or repeated episodes of trauma. Back pain is prominent. Pain is aggravated by activity, sitting, forward bending, and lifting, etc. Pain can be referred into the buttocks, hips, or lower extremities. A systemic response can occur as generalized hypersensitivity or depression.

In Spinal News International (Mar. 22, 2017) it was stated that "when degenerative disc disease is present up to 40% suffer chronic discogenic pain, often with secondary neurologic disorders due to nerve and spinal cord compression and/or chemical irritation."

Prevalence of chronic low back pain today:
  According to The Lancet, low back pain is now the number one cause of disability globally.
  Global disability due to back pain has doubled in the last 25 years.
  Chronic low back pain, which is associated with degenerative disc disease, was the most common non-cancer reason for opioid prescriptions.
  Low back pain does not seem dramatic like cancer or heart attacks but the effects it has on people's livelihoods and ability to work and function surpass every other condition.
  Despite huge investments and over $80 billion per year spent on spine care, there has been no obvious reduction in the prevalence of back pain or disability (USA).
  The most common cause of disability below the age of 45 is chronic low back pain.

SUMMARY

This disclosure relates to a method of treating internal disc disruption or a connective tissue injury, comprising injecting a therapeutic composition into an animal in need thereof, wherein the therapeutic composition comprises transforming growth factor beta 1 (TGF-β1) or transforming growth factor beta 2 (TGF-β2), fibroblast growth factor (FGF), and a pharmaceutically acceptable excipient or a secondary agent.

Some embodiments include a therapeutic composition comprising TGF-β1 or TGF-β2, FGF, water, and at least 2 of the following excipients or secondary agents: dextrose, lidocaine, chondroitin, carboxymethyl cellulose, glucosamine, hyaluronic acid, and a buffer.

DETAILED DESCRIPTION

IDD is painful due to a traumatically induced chemical reaction within the intervertebral disc caused by injury to the nucleus. There is usually fragmentation of part of the nucleus where the fragmented part(s) loses its connection to the vertebral endplate and surrounding tissues. The cells within the fragmented nucleus rupture or become damaged and inflammation ensues. Inflammatory cytokines become manifest. Neutrophils and macrophages may enter the intervertebral disc either via an annular tear or fissure that extends to the periphery of the disc, or a breach of the vertebral endplate giving access to the vertebral body. When an annular tear extends to the outer third of the annulus, sensory nerve endings are exposed. When they come in contact with inflamed nuclear fragments, pain occurs, local or referred.

The pain of IDD is basically due to a chemical reaction within the injured part of the nucleus. A catabolic condition becomes manifest where inflammatory cytokines and matrix degrading enzymes overwhelm the metabolic balance within the disc. When the injured nuclear material migrates into the outer ⅓ of an annular tear, pain is provoked by irritation of peripheral sensory nerves that innervate the outer annulus.

Most conditions of lumbar Internal Disc Disruption become persistently painful and can last for many years to a lifetime. Activities of living and work can be significantly curtailed, causing disability for those most severely affected.

When pain is disabling, treatment is done by interbody fusion. The magnitude of the surgery can be great. Complications are not uncommon. An effective treatment for lumbar Internal Disc Disruption is endoscopic surgery where a 7 mm tube containing a camera and a rongeur to remove damaged nuclear material is placed through the lumbar foramen into the disc. The damaged nuclear material first is identified by injecting the disc with methylene blue which stains the injured nuclear material blue, and then is removed by the rongeur. This procedure requires much skill. The learning curve can require several years to master. Availability is very limited. There are several conditions of IDD where endoscopic surgery cannot be used.

The cause of disc pain is primarily due to an adverse biochemical reaction. It should be possible to treat most of these injuries by intradiscal injection to reduce chemical inflammation and stimulate the disc cells to repair the annulus and nucleus and normalize disc function.

The Spine Journal, Volume 3 Issue 3, May-June 2003 published a pilot study: "Biochemical injection treatment for discogenic low back pain", by Klein, Eek, et al. Thirty patients with chronic intractable low back pain of 8.5 years duration took part in the study. The goal was to identify a biochemical treatment that could provide a physiologic treatment for Degenerative Disc Disease. The purpose was to use agents known to induce proteoglycan synthesis in the treatment of Intervertebral Disc Disease. The lumbar intervertebral discs were injected with a solution of glucosamine and chondroitin sulfate combined with hypertonic dextrose and dimethyl sulfoxide (DMSO). The outcome measures pretreatment were Roland-Morris disability scores and visual analogue scores that were compared with a 1-year follow-up post-test values of these scores. The Roland-Morris and visual analogue scores were significantly less than pre-treatment. The results were statistically significant. These results encouraged further investigation.

It has been discovered that the combination of transforming growth factor and fibroblast growth factor significantly stimulated fibroblasts to manufacture collagen and repair tissue. Therefore, it is felt that the addition of these two components will have a dramatic effect in healing Internal Disc Disruption.

Generally, this disclosure involves injecting, or otherwise administering, a therapeutic composition into an animal, such as a human being, who is suffering from internal disc disruption or a connective tissue injury.

The therapeutic composition can be injected into an intervertebral disc of a patient, e.g., an animal such as a human being, for treatment of internal disc disruption. The therapeutic composition can also be administered to a patient for treatment of connective tissue injuries, such as a connective tissue injury to a knee, shoulder, elbow, wrist, ankle, hip, hand, foot, etc., including connective tissue injury involving a tendon, fascia, ligament, or a joint capsule.

For treatment of internal disc disruption, in some embodiments, the patient is suffering from lumbar internal disc disruption. In some embodiments, the internal disc disruption is a grade 1 disruption. In some embodiments, the internal disc disruption is a grade 2 disruption. In some embodiments, the internal disc disruption is a grade 3 disruption. In some embodiments, the internal disc disruption is a grade 4 disruption.

For treatment of connective tissue injuries, the therapeutic composition is administered, such as by injection, at or near a fibro-periosteal junction of tendon, fascia, ligament, or joint capsule, or at the interface of the connective tissue to periosteum.

The therapeutic composition of the present disclosure comprises transforming growth factor beta 1 (TGF-β1) or transforming growth factor beta 2 (TGF-β2), fibroblast growth factor (FGF), and a pharmaceutically acceptable excipient or a secondary agent.

In some embodiments, the therapeutic composition comprises transforming growth factor TGF-β1, fibroblast growth factor (FGF), and a pharmaceutically acceptable excipient or a secondary agent.

In some embodiments, the therapeutic composition comprises transforming growth factor TGF-β2, fibroblast growth factor (FGF), and a pharmaceutically acceptable excipient or a secondary agent.

Any suitable amount of TGF-β1 may be used in the therapeutic composition, such as about 0.5-40 ng/mL, about 1-20 ng/mL, about 0.5-10 ng/mL, about 10-20 ng/mL, about 20-30 ng/mL, about 30-40 ng/mL, about 0.5-3 ng/mL, about 3-6 ng/mL, about 6-9 ng/mL, about 9-12 ng/mL, about 12-15 ng/mL, about 15-18 ng/mL, about 18-21 ng/mL, about 21-27 ng/mL, about 27-34 ng/mL, or about 34-40 ng/mL. In some embodiments, the concentration of TGF-β1 in the therapeutic composition is about 1-20 ng/mL.

Any suitable amount of TGF-β2 may be used in the therapeutic composition, such as about 0.5-40 ng/mL, about 1-20 ng/mL, about 0.5-10 ng/mL, about 10-20 ng/mL, about 20-30 ng/mL, about 30-40 ng/mL, about 0.5-3 ng/mL, about 3-6 ng/mL, about 6-9 ng/mL, about 9-12 ng/mL, about 12-15 ng/mL, about 15-18 ng/mL, about 18-21 ng/mL, about 21-27 ng/mL, about 27-34 ng/mL, or about 34-40 ng/mL. In some embodiments, the concentration of TGF-β2 in the therapeutic composition is about 1-20 ng/mL.

Any suitable amount of FGF may be used in the therapeutic composition, such as about 20-400 ng/mL, about 50-200 ng/mL, about 20-50 ng/mL, about 50-80 ng/mL, about 80-110 ng/mL, about 110-140 ng/mL, about 140-170 ng/mL, about 170-200 ng/mL, about 200-300 ng/mL, or about 300-400 ng/mL. In some embodiments, the concentration of FGF in the therapeutic composition is about 50-200 ng/mL.

Suitable pharmaceutically acceptable excipients or secondary agents can include, but are not limited to: 1) dextrose, 2) lidocaine, 3) a chondroitin, 4) a carboxymethyl cellulose, 5) a glucosamine, 6) a hyaluronic acid, 7) a phosphate buffer, and 8) water or saline. A pharmaceutical composition may contain at least 1, at least 2, at least 3, at least 4, at least 5, at least 6, at least 7, or all 8 of these pharmaceutically acceptable excipients or secondary agents, as well as others.

Any suitable amount of dextrose may be used in the therapeutic composition, such as about 2-30%, about 5-15%, about 2-10%, about 10-20%, about 20-30%, about 2-5%, about 5-10%, about 10-15%, about 5-7%, about 7-9%, about 9-11%, about 11-13%, or about 13-15% by weight of the therapeutic composition. In some embodiments, the dextrose is about 5-15% of the therapeutic composition.

The therapeutic composition may contain lidocaine, including lidocaine free base and/or any suitable salt form, such as a hydrochloride salt. Any suitable amount of lidocaine (in a free base and/or a salt form, such as a hydrochloride salt) may be used in the therapeutic composition, such as about 0.1-2%, about 0.25-1%, about 0.1-0.25%, about 0.25-0.3%, about 0.3-0.4%, about 0.4-0.5%, about 0.5-0.6%, about 0.6-0.7%, about 0.7-0.8%, about 0.8-0.9%, about 0.9-1%, about 0.25-0.5%, about 0.5-0.75%, about 0.75-1%, about 1-1.5%, or about 1.5-2% by weight of the therapeutic composition. In some embodiments, the lidocaine is about 0.25-1% of the therapeutic composition.

The therapeutic composition may contain chondroitin, including chondroitin in an amine form and/or a salt form, such as a sulfate salt. Any suitable amount of the chondroitin (in an amine and/or a salt form, such as a sulfate salt), may be used in the therapeutic composition, such as about 0.2-4%, about 0.5-2%, about 0.2-0.5%, about 0.5-0.8%, about 0.8-1.1%, about 1.1-1.4%, about 1.4-1.7%, about 1.7-2%, about 0.5-1%, about 1-1.5%, about 1.5-2%, about 2-2.5%, about 2.5-3%, about 3-3.5%, or about 3.5-4% by weight of the therapeutic composition. In some embodiments, the chondroitin, e.g., chondroitin sulfate, is about 0.5-2% of the therapeutic composition.

The therapeutic composition may contain carboxymethyl cellulose, including carboxymethyl cellulose in an acid form and/or a salt form, such as a sodium salt. Any suitable amount of the carboxymethyl cellulose (in an acid and/or a salt form, such as a sodium salt), may be used in the therapeutic composition, such as about 0.01-5%, about 0.01-0.25%, about 0.25-0.5%, about 0.5-1%, about 1-2%, about 2-3%, about 3-4%, or about 4-5% by weight of the therapeutic composition. In some embodiments, the carboxymethyl cellulose, is about 0.01-0.25% of the therapeutic composition.

The therapeutic composition may contain glucosamine, including glucosamine in an amine form and/or a salt form, such as a hydrochloride (HCl) salt. Any suitable amount of the glucosamine (in an amine and/or a salt form, such as a hydrochloride salt (e.g., glucosamine HCl)), may be used in the therapeutic composition, such as about 0.5-12%, about 1-6%, about 0.5-1%, about 1-2%, about 2-3%, about 3-4%, about 4-5%, about 5-6%, about 6-8%, about 8-10%, or about 10-12% by weight of the therapeutic composition. In some embodiments, the glucosamine, e.g., glucosamine HCl, is about 1-6% of the therapeutic composition.

The therapeutic composition may contain hyaluronic acid, including hyaluronic acid in an acid form and/or a salt form, such as a sodium salt. Any suitable amount of the hyaluronic acid (in an acid and/or a salt form, such as a sodium salt), may be used in the therapeutic composition, such as about 0.02-12%, about 0.05-6%, about 0.02-1%, about 1-2%, about 2-3%, about 3-4%, about 4-5%, about 5-6%, about 6-8%, about 8-10%, or about 10-12% by weight of the therapeutic composition. In some embodiments, the hyaluronic acid is about 0.05-6% of the therapeutic composition.

The therapeutic composition may contain a suitable buffer, such as a phosphate buffer. A phosphate buffer may include $PO_4^{3-}$, $HPO_4^{2-}$, $H_2PO_4^-$, or a combination thereof, in a ratio appropriate for the pH of interest. In some embodiments, the therapeutic composition is buffered to a pH of about 5-8, about 5-6, about 6-7, or about 7-8. In some embodiments, the therapeutic composition has a pH of about 6-7.

The therapeutic composition may contain water, including sterile water, or normal saline, in an amount sufficient to provide the concentrations listed above for the other ingredients. For example, the water or saline may be about 60-95% of the therapeutic composition.

In some embodiments, the therapeutic composition comprises dextrose. In some embodiments, the therapeutic composition comprises lidocaine (either in a free base form or a salt form). In some embodiments, the therapeutic composition comprises chondroitin (e.g., in a salt form, such as a sulfate salt, or a free base form). In some embodiments, the therapeutic composition comprises carboxymethyl cellulose (e.g., in an acid form or a salt form, such as a sodium salt). In some embodiments, the therapeutic composition comprises glucosamine (e.g., in a free base or a salt form, such as an HCl salt). In some embodiments, the therapeutic composition comprises hyaluronic acid (e.g., in an acid form or a salt form, such as a sodium salt). In some embodiments, the therapeutic composition comprises phosphate buffer. In some embodiments, the therapeutic composition comprises water or saline.

In some embodiments, the therapeutic composition comprises TGF-β1 or TGF-β2, FGF, dextrose, and lidocaine (either in a free base form or a salt form). In some embodiments, the therapeutic composition comprises TGF-β1 or TGF-β2, FGF, dextrose, and chondroitin (e.g., in a salt form, such as a sulfate salt, or a free base form). In some embodiments, the therapeutic composition comprises TGF-β1 or TGF-β2, FGF, dextrose, and carboxymethyl cellulose (e.g., in an acid form or a salt form, such as a sodium salt). In some embodiments, the therapeutic composition comprises TGF-β1 or TGF-β2, FGF, dextrose, and glucosamine (e.g., in a free base or a salt form, such as an HCl salt). In some embodiments, the therapeutic composition comprises TGF-β1 or TGF-β2, FGF, dextrose, and hyaluronic acid (e.g., in an acid form or a salt form, such as a sodium salt). In some embodiments, the therapeutic composition comprises TGF-β1 or TGF-β2, FGF, dextrose, and phosphate buffer. In some embodiments, the therapeutic composition comprises TGF-β1 or TGF-β2, FGF, dextrose, and water or saline. In some embodiments, the therapeutic composition comprises TGF-β1 or TGF-β2, FGF, lidocaine (either in a free base form or a salt form), and chondroitin (e.g., in a salt form, such as a sulfate salt, or a free base form). In some embodiments, the therapeutic composition comprises TGF-β1 or TGF-β2, FGF, lidocaine (either in a free base form or a salt form), and carboxymethyl cellulose (e.g., in an acid form or a salt form, such as a sodium salt). In some embodiments, the therapeutic composition comprises TGF-β1 or TGF-β2, FGF, lidocaine (either in a free base form or a salt form), and glucosamine (e.g., in a free base or a salt form, such as an HCl salt). In some embodiments, the therapeutic composition comprises TGF-β1 or TGF-β2, FGF, lidocaine (either in a free base form or a salt form), and hyaluronic acid (e.g., in an acid form or a salt form, such as a sodium salt). In some embodiments, the therapeutic composition comprises TGF-β1 or TGF-β2, FGF, lidocaine (either in a free base form or a salt form), and phosphate buffer. In some embodiments, the therapeutic composition comprises TGF-β1 or TGF-β2, FGF, lidocaine (either in a free base form or a salt form), and water or saline. In some embodiments, the therapeutic composition comprises TGF-β1 or TGF-β2, FGF, chondroitin (e.g., in a salt form, such as a sulfate salt, or a free base form), and carboxymethyl cellulose (e.g., in an acid form or a salt form, such as a sodium salt). In some embodiments, the therapeutic composition comprises TGF-β1 or TGF-β2, FGF, hyaluronic acid (e.g., in an acid form or a salt form, such as a sodium salt), and phosphate buffer. In some embodiments, the therapeutic composition comprises TGF-β1 or TGF-β2, FGF, hyaluronic acid (e.g., in an acid form or a salt form, such as a sodium salt), and water or saline.

In some embodiments, the therapeutic composition comprises TGF-β1 or TGF-β2, FGF, chondroitin (e.g., in a salt form, such as a sulfate salt, or a free base form), and glucosamine (e.g., in a free base or a salt form, such as an HCl salt). In some embodiments, the therapeutic composition comprises TGF-β1 or TGF-β2, FGF, chondroitin (e.g., in a salt form, such as a sulfate salt, or a free base form), and hyaluronic acid (e.g., in an acid form or a salt form, such as a sodium salt). In some embodiments, the therapeutic composition comprises TGF-β1 or TGF-β2, FGF, chondroitin (e.g., in a salt form, such as a sulfate salt, or a free base form), and phosphate buffer. In some embodiments, the therapeutic composition comprises TGF-β1 or TGF-β2, FGF, chondroitin (e.g., in a salt form, such as a sulfate salt, or a free base form), and water or saline. In some embodiments, the therapeutic composition comprises TGF-β1 or TGF-β2, FGF, carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1 or TGF-β2, FGF, carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1 or TGF-β2, FGF, carboxymethyl cellulose (e.g., in an acid form or a salt form, such as a sodium salt), and phosphate buffer. In some embodiments, the therapeutic composition comprises TGF-β1 or TGF-β2, FGF, carboxymethyl cellulose (e.g., in an acid form or a salt form, such as a sodium salt), and water or saline. In some embodiments, the therapeutic composition comprises TGF-β1 or TGF-β2, FGF, glucosamine (e.g., in a free base or a salt form, such as an HCl salt), and hyaluronic acid (e.g., in an acid form or a salt form, such as a sodium salt). In some embodiments, the therapeutic composition comprises TGF-β1 or TGF-β2, FGF, glucosamine (e.g., in a free base or a salt form, such as an HCl salt), and phosphate buffer. In some embodiments, the therapeutic composition comprises TGF-β1 or TGF-β2, FGF, glucosamine (e.g., in a free base or a salt form, such as an HCl salt), and water or saline. In some embodiments, the therapeutic composition comprises TGF-β1 or TGF-β2, FGF, phosphate buffer, and water or saline.

In some embodiments, the therapeutic composition comprises TGF-β1 or TGF-β2, FGF, dextrose, lidocaine (either in a free base form or a salt form), and chondroitin (e.g., in a salt form, such as a sulfate salt, or a free base form). In some embodiments, the therapeutic composition comprises TGF-β1 or TGF-β2, FGF, dextrose, lidocaine (either in a free base form or a salt form), and carboxymethyl cellulose (e.g., in an acid form or a salt form, such as a sodium salt). In some embodiments, the therapeutic composition comprises TGF-β1 or TGF-β2, FGF, dextrose, lidocaine (either in a free base form or a salt form), and glucosamine (e.g., in a free base or a salt form, such as an HCl salt). In some embodiments, the therapeutic composition comprises TGF-β1 or TGF-β2, FGF, dextrose, lidocaine (either in a free base form or a salt form), and hyaluronic acid (e.g., in an acid form or a salt form, such as a sodium salt). In some embodiments, the therapeutic composition comprises TGF-β1 or TGF-β2, FGF, dextrose, lidocaine (either in a free base form or a salt form), and phosphate buffer. In some embodiments, the therapeutic composition comprises TGF-β1 or TGF-β2, FGF, dextrose, lidocaine (either in a free base form or a salt form), and water or saline. In some embodiments, the therapeutic composition comprises TGF-β1 or TGF-β2, FGF, dextrose, chondroitin (e.g., in a salt form, such as a sulfate salt, or a free base form), and carboxymethyl cellulose (e.g., in an acid form or a salt form, such as a sodium salt). In some embodiments, the therapeutic composition comprises TGF-β1 or TGF-β2, FGF, dextrose, chondroitin (e.g., in a salt form, such as a sulfate salt, or a free base form), and glucosamine (e.g., in a free base or a salt form, such as an HCl salt). In some embodiments, the therapeutic composition comprises TGF-β1 or TGF-β2, FGF, dextrose, chondroitin (e.g., in a salt form, such as a sulfate salt, or a free base form), and hyaluronic acid (e.g., in an acid form or a salt form, such as a sodium salt). In some embodiments, the therapeutic composition comprises TGF-β1 or TGF-β2, FGF, dextrose, chondroitin (e.g., in a salt form, such as a sulfate salt, or a free base form), and phosphate buffer. In some embodiments, the therapeutic composition comprises TGF-β1 or TGF-β2, FGF, dextrose, chondroitin (e.g., in a salt form, such as a sulfate salt, or a free base form), and water or saline. In some embodiments, the therapeutic composition comprises TGF-β1 or TGF-β2, FGF, dextrose, carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1 or TGF-β2, FGF, dextrose, carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1 or TGF-β2, FGF, dextrose, carboxymethyl cellulose (e.g., in an acid form or a salt form, such as a sodium salt), and phosphate buffer. In some embodiments, the therapeutic composition comprises TGF-β1 or TGF-β2, FGF, dextrose, carboxymethyl cellulose (e.g., in an acid form or a salt form, such as a sodium salt), and water or saline. In some embodiments, the therapeutic composition comprises TGF-β1 or TGF-β2, FGF, dextrose, glucosamine (e.g., in a free base or a salt form, such as an HCl salt), and hyaluronic acid (e.g., in an acid form or a salt form, such as a sodium salt). In some embodiments, the therapeutic composition comprises TGF-β1 or TGF-β2, FGF, dextrose, glucosamine (e.g., in a free base or a salt form, such as an HCl salt), and phosphate buffer. In some embodiments, the therapeutic composition comprises TGF-β1 or TGF-β2, FGF, dextrose, glucosamine (e.g., in a free base or a salt form, such as an HCl salt), and water or saline. In some embodiments, the therapeutic composition comprises TGF-β1 or TGF-β2, FGF, dextrose, hyaluronic acid (e.g., in an acid form or a salt form, such as a sodium salt), and phosphate buffer. In some embodiments, the therapeutic composition comprises TGF-β1 or TGF-β2, FGF, dextrose, hyaluronic acid (e.g., in an acid form or a salt form, such as a sodium salt), and water or saline. In some embodiments, the therapeutic composition comprises TGF-β1 or TGF-β2, FGF, dextrose, phosphate buffer, and water or saline. In some embodiments, the therapeutic composition comprises TGF-β1 or TGF-β2, FGF, lidocaine (either in a free base form or a salt form), chondroitin (e.g., in a salt form, such as a sulfate salt, or a free base form), and carboxymethyl cellulose (e.g., in an acid form or a salt form, such as a sodium salt). In some embodiments, the therapeutic composition comprises TGF-β1 or TGF-β2, FGF, lidocaine (either in a free base form or a salt form), chondroitin (e.g., in a salt form, such as a sulfate salt, or a free base form), and glucosamine (e.g., in a free base or a salt form, such as an HCl salt). In some embodiments, the therapeutic composition comprises TGF-β1 or TGF-β2, FGF, lidocaine (either in a free base form or a salt form), chondroitin (e.g., in a salt form, such as a sulfate salt, or a free base form), and hyaluronic acid (e.g., in an acid form or a salt form, such as a sodium salt). In some embodiments, the therapeutic composition comprises TGF-β1 or TGF-β2, FGF, lidocaine (either in a free base form or a salt form), chondroitin (e.g., in a salt form, such as a sulfate salt, or a free base form), and phosphate buffer. In some embodiments, the therapeutic composition comprises TGF-β1 or TGF-β2, FGF, lidocaine (either in a free base form or a salt form), chondroitin (e.g., in a salt form, such as a sulfate salt, or a free base form), and water or saline. In some embodiments, the therapeutic composition comprises TGF-β1 or TGF-β2, FGF, lidocaine (either in a free base form or a salt form), carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1 or TGF-β2, FGF, lidocaine (either in a free base form or a salt form), carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1 or TGF-β2, FGF, lidocaine (either in a free base form or a salt form), carboxymethyl cellulose (e.g., in an acid form or a salt form, such as a sodium salt), and phosphate buffer. In some embodiments, the therapeutic composition comprises TGF-β1 or TGF-β2, FGF, lidocaine (either in a free base form or a salt form), carboxymethyl cellulose (e.g., in an acid form or a salt form, such as a sodium salt), and water or saline. In some embodiments, the therapeutic composition comprises TGF-β1 or TGF-β2, FGF, lidocaine (either in a free base form or a salt form), glucosamine (e.g., in a free base or a salt form, such as an HCl salt), and hyaluronic acid (e.g., in an acid form or a salt form, such as a sodium salt). In some embodiments, the therapeutic composition comprises TGF-β1 or TGF-β2, FGF, lidocaine (either in a free base form or a salt form), glucosamine (e.g., in a free base or a salt form, such as an HCl salt), and phosphate buffer. In some embodiments, the therapeutic composition comprises TGF-β1 or TGF-β2, FGF, lidocaine (either in a free base form or a salt form), glucosamine (e.g., in a free base or a salt form, such as an HCl salt), and water or saline. In some embodiments, the therapeutic composition comprises TGF-β1 or TGF-β2, FGF, lidocaine (either in a free base form or a salt form), hyaluronic acid (e.g., in an acid form or a salt form, such as a sodium salt), and phosphate buffer. In some embodiments, the therapeutic composition comprises TGF-β1 or TGF-β2, FGF, lidocaine (either in a free base form or a salt form), hyaluronic acid (e.g., in an acid form or a salt form, such as a sodium salt), and water or saline. In some embodiments, the therapeutic composition comprises TGF-β1 or TGF-β2, FGF, lidocaine (either in a free base form or a salt form), phosphate buffer, and water or saline. In some embodiments, the therapeutic composition comprises TGF-β1 or TGF-β2, FGF, chondroitin (e.g., in a salt form, such as a sulfate salt, or a free base form), carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1 or TGF-β2, FGF, chondroitin (e.g., in a salt form, such as a sulfate salt, or a free base form), carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1 or TGF-β2, FGF, chondroitin (e.g., in a salt form, such as a sulfate salt, or a free base form), carboxymethyl cellulose (e.g., in an acid form or a salt form, such as a sodium salt), and phosphate buffer. In some embodiments, the therapeutic composition comprises TGF-β1 or TGF-β2, FGF, chondroitin (e.g., in a salt form, such as a sulfate salt, or a free base form), carboxymethyl cellulose (e.g., in an acid form or a salt form, such as a sodium salt), and water or saline. In some embodiments, the therapeutic composition comprises TGF-β1 or TGF-β2, FGF, chondroitin (e.g., in a salt form, such as a sulfate salt, or a free base form), glucosamine (e.g., in a free base or a salt form, such as an HCl salt), and hyaluronic acid (e.g., in an acid form or a salt form, such as a sodium salt). In some embodiments, the therapeutic composition comprises TGF-β1 or TGF-β2, FGF, chondroitin (e.g., in a salt form, such as a sulfate salt, or a free base form), glucosamine (e.g., in a free base or a salt form, such as an HCl salt), and phosphate buffer. In some embodiments, the therapeutic composition comprises TGF-β1 or TGF-β2, FGF, chondroitin (e.g., in a salt form, such as a sulfate salt, or a free base form), glucosamine (e.g., in a free base or a salt form, such as an HCl salt), and water or saline. In some embodiments, the therapeutic composition comprises TGF-β1 or TGF-β2, FGF, chondroitin (e.g., in a salt form, such as a sulfate salt, or a free base form), hyaluronic acid (e.g., in an acid form or a salt form, such as a sodium salt), and phosphate buffer. In some embodiments, the therapeutic composition comprises TGF-β1 or TGF-β2, FGF, chondroitin (e.g., in a salt form, such as a sulfate salt, or a free base form), hyaluronic acid (e.g., in an acid form or a salt form, such as a sodium salt), and water or saline. In some embodiments, the therapeutic composition comprises TGF-β1 or TGF-β2, FGF, chondroitin (e.g., in a salt form, such as a sulfate salt, or a free base form), phosphate buffer, and water or saline. In some embodiments, the therapeutic composition comprises TGF-β1 or TGF-β2, FGF, carboxymethyl cellulose (e.g., in an acid form or a salt form, such as a sodium salt), glucosamine (e.g., in a free base or a salt form, such as an HCl salt), and hyaluronic acid (e.g., in an acid form or a salt form, such as a sodium salt). In some embodiments, the therapeutic composition comprises TGF-β1 or TGF-β2, FGF, carboxymethyl cellulose (e.g., in an acid form or a salt form, such as a sodium salt), glucosamine (e.g., in a free base or a salt form, such as an HCl salt), and phosphate buffer. In some embodiments, the therapeutic composition comprises TGF-β1 or TGF-β2, FGF, carboxymethyl cellulose (e.g., in an acid form or a salt form, such as a sodium salt), glucosamine (e.g., in a free base or a salt form, such as an HCl salt), and water or saline. In some embodiments, the therapeutic composition comprises TGF-β1 or TGF-β2, FGF, carboxymethyl cellulose (e.g., in an acid form or a salt form, such as a sodium salt), hyaluronic acid (e.g., in an acid form or a salt form, such as a sodium salt), and phosphate buffer. In some embodiments, the therapeutic composition comprises TGF-β1 or TGF-β2, FGF, carboxymethyl cellulose (e.g., in an acid form or a salt form, such as a sodium salt), hyaluronic acid (e.g., in an acid form or a salt form, such as a sodium salt), and water or saline. In some embodiments, the therapeutic composition comprises TGF-β1 or TGF-β2, FGF, carboxymethyl cellulose (e.g., in an acid form or a salt form, such as a sodium salt), phosphate buffer, and water or saline. In some embodiments, the therapeutic composition comprises TGF-β1 or TGF-β2, FGF, glucosamine (e.g., in a free base or a salt form, such as an HCl salt), hyaluronic acid (e.g., in an acid form or a salt form, such as a sodium salt), and phosphate buffer. In some embodiments, the therapeutic composition comprises TGF-β1 or TGF-β2, FGF, glucosamine (e.g., in a free base or a salt form, such as an HCl salt), hyaluronic acid (e.g., in an acid form or a salt form, such as a sodium salt), and water or saline. In some embodiments, the therapeutic composition comprises TGF-β1 or TGF-β2, FGF, glucosamine (e.g., in a free base or a salt form, such as an HCl salt), phosphate buffer, and water or saline.

In some embodiments, the therapeutic composition comprises TGF-β1 or TGF-β2, FGF, lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g. in a free base or a salt form, such as an HCl salt), hyaluronic acid (e.g. in an acid form or a salt form, such as a sodium salt), phosphate buffer, and water or saline. In some embodiments, the therapeutic composition comprises TGF-β1 or TGF-β2, FGF, dextrose, chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), phosphate buffer, and water or saline. In some embodiments, the therapeutic composition comprises TGF-β1 or TGF-β2, FGF, dextrose, lidocaine (either in a free base form or a salt form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), phosphate buffer, and water or saline. In some embodiments, the therapeutic composition comprises TGF-β1 or TGF-β2, FGF, dextrose, lidocaine (either in a free base form or a salt form), chondroitin (e.g., in a salt form, such as a sulfate salt, or a free base form), glucosamine (e.g., in a free base or a salt form, such as an HCl salt), hyaluronic acid (e.g., in an acid form or a salt form, such as a sodium salt), phosphate buffer, and water or saline. In some embodiments, the therapeutic composition comprises TGF-β1 or TGF-β2, FGF, dextrose, lidocaine (either in a free base form or a salt form), chondroitin (e.g., in a salt form, such as a sulfate salt, or a free base form), carboxymethyl cellulose (e.g., in an acid form or a salt form, such as a sodium salt), hyaluronic acid (e.g., in an acid form or a salt form, such as a sodium salt), phosphate buffer, and water or saline. In some embodiments, the therapeutic composition comprises TGF-β1 or TGF-β2, FGF, dextrose, lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), phosphate buffer, and water or saline. In some embodiments, the therapeutic composition comprises TGF-β1 or TGF-β2, FGF, dextrose, lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g. in an acid form or a salt form, such as a sodium salt), and water or saline. In some embodiments, the therapeutic composition comprises TGF-β1 or TGF-β2, FGF, dextrose, lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), and phosphate buffer.

In some embodiments, the therapeutic composition comprises TGF-β1 or TGF-β2, FGF, dextrose, chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), and phosphate buffer saline.

In some embodiments, the therapeutic composition comprises:
1. Transforming growth factor beta 1 (TGF-β1) 1 ng/mL to 20 ng/mL
2. Fibroblast growth factor (FGF) 50 ng/mL to 200 ng/mL
3. Dextrose 5%-15%
4. Lidocaine 0.25%-1%
5. Chondroitin sulfate 0.5%-2%
6. Carboxymethyl cellulose
7. Glucosamine HCL 1%-6%
8. Hyaluronic acid 0.05%-6%
9. Phosphate buffers, pH 6-7
10. Water QS (sterile water or normal saline QS)

In some embodiments, the therapeutic composition comprises:
1. Transforming growth factor beta 2 (TGF-β2) 1 ng/mL to 20 ng/mL
2. Fibroblast growth factor (FGF) 50 ng/mL to 200 ng/mL
3. Dextrose 5%-15%
4. Lidocaine 0.25%-1%
5. Chondroitin sulfate 0.5%-2%
6. Carboxymethyl cellulose
7. Glucosamine HCL 1%-6%
8. Hyaluronic acid 0.05%-6%
9. Phosphate buffers, pH 6-7
10. Water QS (sterile water or normal saline QS)

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A therapeutic composition comprising Transforming growth factor beta 1 (TGF-β1) or Transforming growth factor beta 1 (TGF-β2), about 20 ng/ml to about 400 ng/mL Fibroblast growth factor (FGF), about 0.05% to about 6% hyaluronic acid by weight, water, and at least 2 of the following excipients or secondary agents: dextrose, lidocaine, chondroitin, carboxymethyl cellulose, glucosamine, and a buffer.

2. The therapeutic composition of claim 1, comprising TGF-β1.

3. The therapeutic composition of claim 1, comprising TGF-β2.

4. The therapeutic composition of claim 1, comprising at least 3 of the following excipients or secondary agents: dextrose, lidocaine, chondroitin, carboxymethyl cellulose, glucosamine, and the buffer.

5. The therapeutic composition of claim 1, comprising at least 4 of the following excipients or secondary agents: dextrose, lidocaine, chondroitin, carboxymethyl cellulose, glucosamine, and the buffer.

6. The therapeutic composition of claim 1, comprising at least 5 of the following excipients or secondary agents: dextrose, lidocaine, chondroitin, carboxymethyl cellulose, glucosamine, and the buffer.

7. The therapeutic composition of claim 1, comprising at least 6 of the following excipients or secondary agents: dextrose, lidocaine, chondroitin, carboxymethyl cellulose, glucosamine, and the buffer.

8. The therapeutic composition of claim 1, comprising dextrose, lidocaine, chondroitin, carboxymethyl cellulose, glucosamine, and the buffer.

9. The therapeutic composition of claim 1, comprising about 1 ng/ml to 20 ng/ml of TGF-β1.

10. The therapeutic composition of claim 1, comprising about 1 ng/ml to 20 ng/ml of TGF-β2.

11. The therapeutic composition of claim 1, comprising about 50 ng/ml to 200 ng/ml of FGF.

12. The therapeutic composition of claim 1, comprising about 5% to about 15% dextrose.

13. The therapeutic composition of claim 1, comprising about 0.25% to about 1% lidocaine.

14. The therapeutic composition of claim 1, comprising about 0.5% to about 2% chondroitin sulfate.

15. The therapeutic composition of claim 1, comprising about 1% to about 6% glucosamine HCl.

16. The therapeutic composition of claim 1, comprising about 0.05% to about 6% hyaluronic acid.

17. The therapeutic composition of claim 1, which is buffered to a pH of about 6 to about 7, wherein the buffer comprises a phosphate buffer.

* * * * *